(12) United States Patent
Sasamoto et al.

(10) Patent No.: US 9,664,624 B2
(45) Date of Patent: May 30, 2017

(54) DEVICE FOR TESTING APPLICATION STATE OF FIBER REINFORCED PLASTIC TAPE

(71) Applicant: TORAY ENGINEERING CO., LTD., Chuo-ku, Tokyo (JP)

(72) Inventors: Hiromichi Sasamoto, Otsu (JP); Hisashi Kobayashi, Otsu (JP); Yoshio Nogami, Kuwana (JP)

(73) Assignee: TORAY ENGINEERING CO., LTD., Tokyo (JP)

( * ) Notice: Subject to any disclaimer, the term of this patent is extended or adjusted under 35 U.S.C. 154(b) by 365 days.

(21) Appl. No.: 14/419,551

(22) PCT Filed: May 27, 2013

(86) PCT No.: PCT/JP2013/064575
§ 371 (c)(1),
(2) Date: Feb. 4, 2015

(87) PCT Pub. No.: WO2014/024543
PCT Pub. Date: Feb. 13, 2014

(65) Prior Publication Data
US 2015/0212008 A1 Jul. 30, 2015

(30) Foreign Application Priority Data
Aug. 7, 2012 (JP) ................................. 2012-174494

(51) Int. Cl.
*G01N 21/86* (2006.01)
*G01N 21/88* (2006.01)
(Continued)

(52) U.S. Cl.
CPC ......... *G01N 21/86* (2013.01); *G01N 21/8806* (2013.01); *G01N 21/8851* (2013.01);
(Continued)

(58) Field of Classification Search
CPC ............... G01N 21/86; G01N 21/8851; G01N 21/8806; G01N 21/952; G01N 21/892;
(Continued)

(56) References Cited

U.S. PATENT DOCUMENTS

| 2007/0223802 A1* | 9/2007 | Tateda | B29C 70/54 382/141 |
| 2007/0229805 A1* | 10/2007 | Engelbart | B29C 70/32 356/237.1 |
| 2013/0194568 A1* | 8/2013 | Hatsuda | G01N 21/88 356/237.3 |

FOREIGN PATENT DOCUMENTS

| JP | 09-289373 A | 11/1997 | |
| JP | 4691562 B | * 11/2005 | ............. G01B 11/14 |

(Continued)

OTHER PUBLICATIONS

International Search Report of the corresponding International Application No. PCT/JP2013/064575, dated Jun. 25, 2013.

*Primary Examiner* — Sath V Perungavoor
*Assistant Examiner* — Howard D Brown, Jr.
(74) *Attorney, Agent, or Firm* — Global IP Counselors, LLP

(57) ABSTRACT

A device for testing an application state of a plurality of strips of fiber reinforced plastic tape affixed in rows on a surface of a structure, the device includes an illumination component emits observation-use illuminating light beams toward a test region of the fiber reinforced plastic tape, an observation component observes reflected light from the test region, and a testing component tests the application state of the fiber reinforced plastic tape based on an image observed by the observation component. The illumination component includes a plurality of irradiation units that light simultaneously and are disposed such that a pair of the observation-use illuminating light beams are emitted from directions that
(Continued)

are mutually symmetrical with respect to a normal line of the test region, and an illumination direction change component that changes the directions of the pair of observation-use illuminating light beams emitted from the illumination component about the normal line.

20 Claims, 9 Drawing Sheets

(51) Int. Cl.
    *G01N 21/892*     (2006.01)
    *G01N 21/952*     (2006.01)
    *G06T 7/00*     (2017.01)

(52) U.S. Cl.
    CPC ......... *G01N 21/892* (2013.01); *G01N 21/952* (2013.01); *G06T 7/0004* (2013.01); *G01N 2201/02* (2013.01); *G01N 2201/061* (2013.01)

(58) Field of Classification Search
    CPC ......... G01N 2201/02; G01N 2201/061; G01N 21/88; G06T 7/0004; H04N 7/18; B65B 19/28; G01B 11/022
    See application file for complete search history.

(56) References Cited

FOREIGN PATENT DOCUMENTS

| | | |
|---|---|---|
| JP | 2007-256119 A | 10/2007 |
| JP | 2009-531715 A | 9/2009 |
| JP | 4691562 B2 | 6/2011 |
| JP | 2011-196897 A | 10/2011 |
| WO | 2007-126891 A1 | 11/2007 |

\* cited by examiner

DEVICE FOR TESTING APPLICATION STATE OF FIBER REINFORCED PLASTIC TAPE

CROSS-REFERENCE TO RELATED APPLICATIONS

This application is a U.S. National stage of International Application No. PCT/JP2013/064575 filed on May 27, 2013. This application claims priority to Japanese Patent Application No. 2012-174494 filed with Japan Patent Office on Aug. 7, 2012. The entire disclosure of Japanese Patent Application No. 2012-174494 is hereby incorporated herein by reference.

BACKGROUND

Field of the Invention

The present invention relates to a device for testing the application state of a plurality of strips of fiber reinforced plastic tape affixed in rows on the surface of a structure.

Background Information

Fiber reinforced plastic sheets have been used in recent years in sports applications and in aerospace applications that require a lightweight and high-performance structure. Many sheet-like molding intermediate materials in a semi-cured state in which carbon fiber has been impregnated with a thermoplastic resin, which is called prepreg, have been used in aerospace applications in particular. This prepreg is formed by making a multilayer laminate on a structure and then curing with heat.

When a curved surface such as a cylinder, typified by an aircraft fuselage, is formed, if a prepreg in the form of a wide sheet is applied so as to conform to the surface shape of a curved structure, the prepreg tends to wrinkle. Accordingly, when prepregs are affixed and laminated on a curved surface, the sheet is appropriately sated and applied in the form of narrow strips of tape, which are evenly laminated and built up.

Also, the strength of a prepreg is different in the direction in which the fibers extend and in the direction intersecting these fibers. Therefore, when a prepreg is applied and laminated over the fuselage portion of an aircraft, the orientation of a layer is always changed by at least 45 degrees from that of the underlying layer so that the direction in which the fibers extend will be vertical, diagonal, horizontal, diagonal, and so on, and this lamination involves from about 50 to 100 layers. Also, anywhere from a few strips to about 50 strips of prepreg are generally applied all at once for a single layer.

The prepregs applied in the form of narrow strips of tape as discussed above are tested for their application state, such as whether they are arranged at a specific spacing from each other, or overlapping each other, etc.

This test is sometimes performed automatically while the prepregs are being applied (see Japanese Patent No. 4,691,562 (Patent Literature 1) and Japanese Translation of PCT International Application Publication No. 2009-531715 (Patent Literature 2), for example), but uneven positioning of the front and rear ends where the prepreg is applied, or the adhesion of foreign matter that may occur due to problems along the supply path could not be tested for. Accordingly, it was essential for a human to visually inspect the result after each layer was finished being applied.

SUMMARY

However, when the test object is an aircraft fuselage or the like, and dozens of prepreg layers are laminated, when the lamination is performed by continuously varying the direction of the prepreg fibers in various ways, such as when at a certain level the fibers are oriented longitudinally, then diagonally at the next layer, then laterally at the next layer, steps can be generated by the gaps between one strip of tape and the one underneath, for example, and consequently, in visual testing by a human, numerous problems may be encountered in terms of ensuring the tester has enough experience, speeding up how long the test takes, attaining good reproducibility in the test quality, and so forth.

The present invention was conceived in light of the above situation, and it is an object thereof to provide a device that tests the application state of a plurality of strips of fiber reinforced plastic tape affixed in rows on the surface of a structure, while doing this automatically and quickly and preserving the reproducibility of the test quality.

To solve the above problem, the invention according to a first aspect is a device for testing the application state of a plurality of strips of fiber reinforced plastic tape affixed in rows on the surface of a structure, the device comprising:

an illumination component that emits observation-use illuminating light beams toward the test region of the fiber reinforced plastic tape;

an observation component that observes reflected light from the test region; and a testing component that tests the application state of the fiber reinforced plastic tape based on an image observed by the observation component, wherein the illumination component is configured to include a plurality of irradiation units that light simultaneously, the irradiation units that light simultaneously are disposed so that a pair of observation-use illuminating light beams are emitted from directions that are mutually symmetrical with respect to a normal line of the test region, and the illumination component comprises an illumination direction change component that changes the direction of the pair of observation-use illuminating light beams emitted from the illumination component about the normal line.

The invention according to a second aspect is the device for testing the application state of fiber reinforced plastic tape according to the first aspect, comprising a relative movement component that keeps the distance between the observation component and the surface of the structure constant while relatively moving the observation site of the observation component with respect to the structure.

The invention according to a third aspect is the device for testing the application state of fiber reinforced plastic tape according to the first or second aspect, wherein the plurality of irradiation units that light simultaneously are disposed so as to emit observation-use illuminating light beams in at least two directions toward the test region, the illumination direction change component further comprises an illumination holder that fixes and holds the irradiation units that light simultaneously at a specific angle, and the illumination holder comprises an illumination holder rotation component that rotates the irradiation units that light simultaneously around the normal line.

The invention according to a fourth aspect is the device for testing the application state of fiber reinforced plastic tape according to the first or second aspect, wherein the illumination component is disposed so as to emit light in all peripheral directions with respect to the normal line, toward the test region, the illumination direction change component further comprises a switching component that selectively lights the plurality of irradiation units that light simultaneously, and the switching component switches the observation-use illuminating light beams by selecting at least two specific directions from among all the peripheral directions.

The invention according to a fifth aspect is the device for testing the application state of fiber reinforced plastic tape according to any one of the second to fourth aspects, comprising an image recorder that records images observed by the observation component, wherein the relative movement component comprises a position sensor that senses the observation site of the observation component with respect to the structure, the illumination direction change component comprises an illumination direction sensor, the device comprises a continuous observation controller that changes the illumination direction and observes an image continuously while relatively moving the observation site of the observation component with respect to the structure, and the device comprises a grouping test function that groups and tests continuously observed images that have the same direction of emission of the observation-use illuminating light beams.

The invention according to a sixth aspect is the device for testing the application state of fiber reinforced plastic tape according to any one of the first to fifth aspects, wherein the observation-use illuminating light beams includes light with a wavelength of at least 600 nm, and out of the reflected light, the observation component observes light with a wavelength of at least 600 nm.

The invention according to a seventh aspect is the device for testing the application state of fiber reinforced plastic tape according to the sixth aspect, wherein the observation component comprises a filter that attenuates light with a wavelength of 600 nm or less, out of the reflected light.

The invention according to an eighth aspect is the device for testing the application state of fiber reinforced plastic tape according to any one of the first to seventh aspects, wherein the observation component further comprises a polarizing filter and a polarizing filter holder that holds the polarizing filter, and the polarizing filter holder comprises a polarization direction adjustment component that adjusts the polarization direction of the polarizing filter to around the observation optical axis of the observation camera.

The invention according to a ninth aspect is the device for testing the application state of fiber reinforced plastic tape according to the eighth aspect, further comprising a function for indicating a defect position, for test categories in the testing component.

Illuminating light is emitted in a direction suited to the fiber direction of the fiber reinforced plastic tape, so it is unaffected by the fiber direction of an underlying layer, can testing can focus on the application state of the tape in the top layer.

Accordingly, testing of a lamination state can be automated, without relying on a human worker, so testing accuracy can be increased and testing expense and duration can be reduced.

DETAILED DESCRIPTION OF EMBODIMENTS

Figure 1:
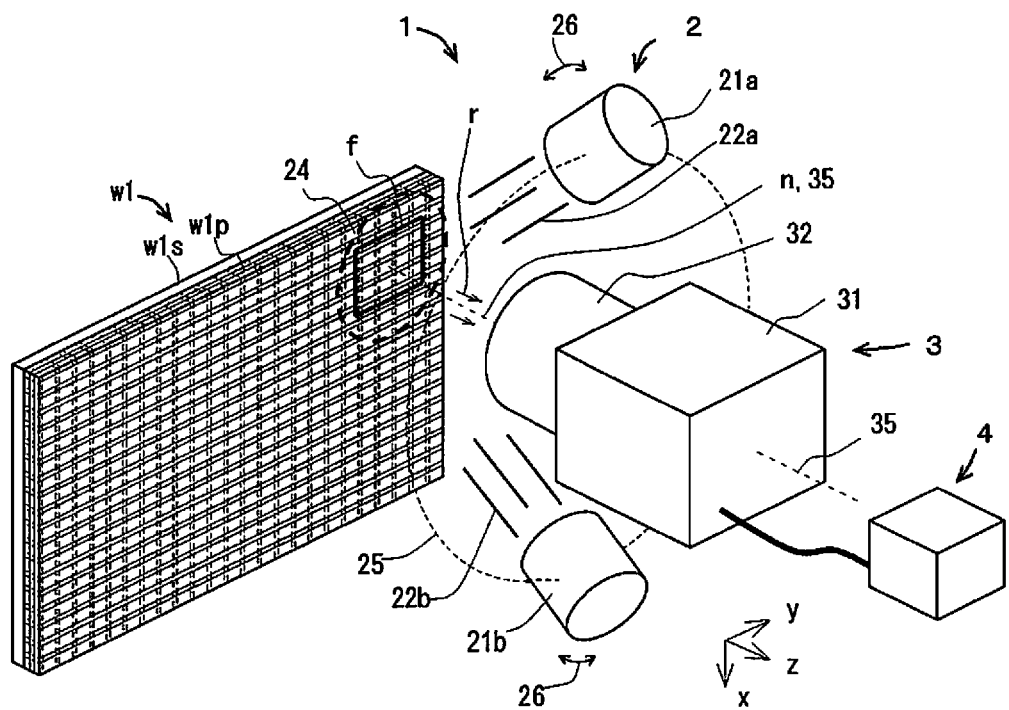
FIG. 1 is an oblique view of the simplified configuration of the test device pertaining to the present invention.

The device (hereinafter referred to as test device) pertaining to the present invention for testing the application state of fiber reinforced plastic tape (hereinafter also referred to simply as tape) will now be described through reference to FIG. 1. In the drawing, we will let the test region faces of the test object represent the X and Y directions, and let the tape thickness direction that is perpendicular to these directions represent the Z direction (the same applies hereinafter).

FIG. 1 is an oblique view of the simplified configuration of the test device pertaining to the present invention, and illustrates one embodiment of testing a structure w1 that is a flat test object (hereinafter referred to as the test object). This test object w1 is produced by laminating a number of layers of fiber reinforced plastic tape w1p over the surface of a structure w1s while varying the direction of the tape.

A test device 1 comprises an illumination component 2, an observation component 3, and a testing component 4. The test device 1 is used to test the application state of a plurality of strips of fiber reinforced plastic tape applied in rows on the surface of the test object w1.

The illumination component 2 is configured to include a plurality of irradiation units 21a and 21b and light source units (not shown) that light these simultaneously. The irradiation units 21a and 21b emit observation-use illuminating light beams 22a and 22b toward a test region f of the fiber reinforced plastic tape (the test object), and are disposed so that uniform light will be emitted at a specific angle from specific directions at an illuminating light illumination region 24, which is wider than the test region f. More specifically, the irradiation units 21a and 21b can be LED lights or halogen lights, for example, but can also be laser lights or some other light source that emits visible light beams, ultraviolet light beams, or infrared light beams, for example.

The observation component 3 is configured to include an observation camera 31 and a lens 32. The observation component 3 observes reflected light r from the test region f. The "reflected light r" referred to here also includes what is known as the scattered component of light. The observation camera 31 outputs an observation image to the testing component 4, which will be described in detail below. More specifically, an example of the observation camera 31 is one equipped with an area image sensor, typified by a CCD or a CMOS. The lens 32 projects an image of the test region f set on the surface of the test object w1 onto the area image sensor of the observation camera 31. More specifically, the lens 32 can be one equipped with a combination of a plurality of convex or concave lenses, and examples include commonly available CCTV or telecentric lenses, and object lenses of optical microscopes.

Figure 2:
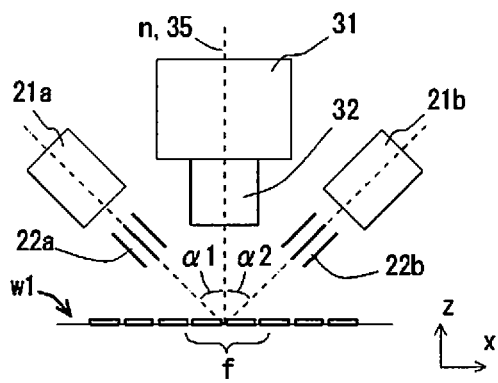
FIG. 2 is a diagram of the layout of the illumination component and the observation component of the test device pertaining to the present invention.

FIG. 2 is a diagram of the layout of the illumination component and the observation component of the test device pertaining to the present invention, and shows the illumination component 2 and the observation component 3 of the test device 1 shown in FIG. 1, as seen from the Y direction.

The irradiation units 21a and 21b that light simultaneously are disposed so as to emit a pair of observation-use illuminating light beams 22a and 22b from directions (a1 and a2 in the drawing) that are mutually symmetrical with respect to a normal line n of the test region f set on the test object w1.

Figure 3:
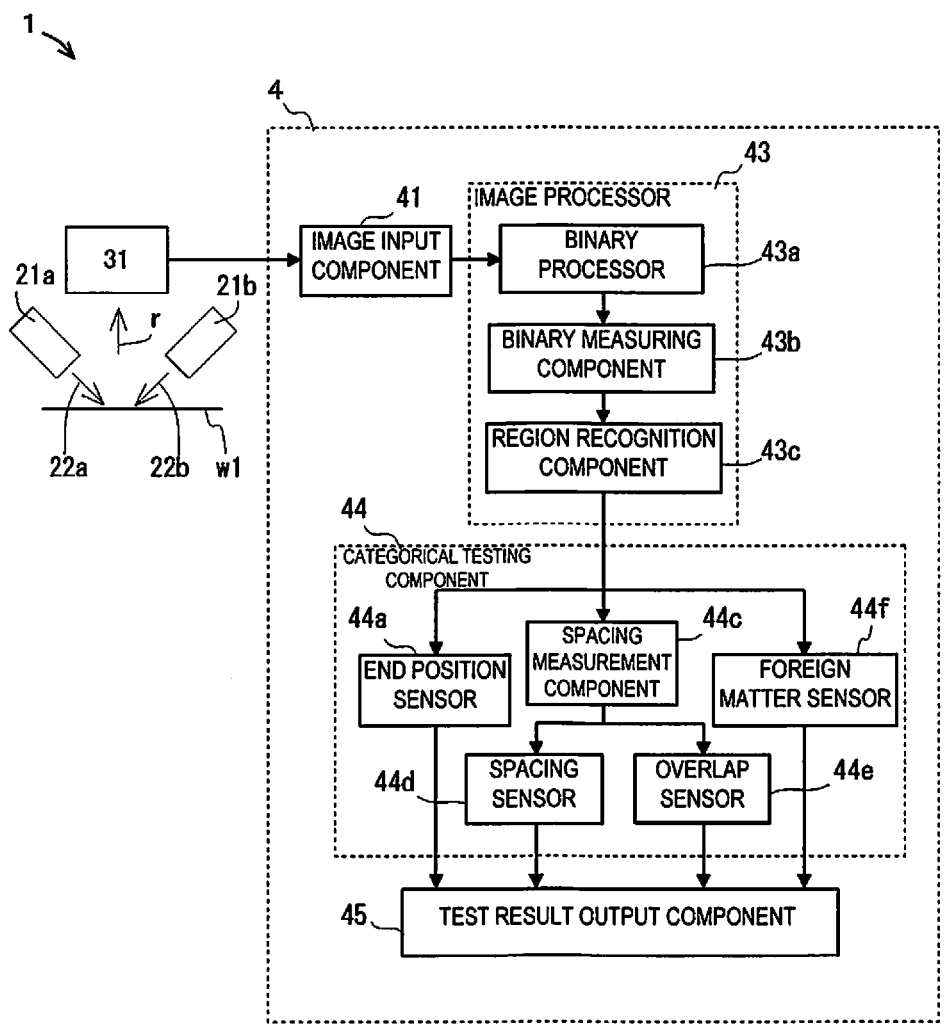
FIG. 3 is a block diagram of the test device pertaining to the present invention.

FIG. 3 is a block diagram of the test device pertaining to the present invention, and shows in detail the various components constituting the test device 1.

The testing component 4 will be discussed in detail below, but comprises an image input component 41, an image processor 43, a categorical testing component 44, and a test result output component 45. The testing component 4 tests the application state of the above-mentioned fiber reinforced plastic tape based on the image observed by the observation camera 31. The various components will be discussed in detail below.

More specifically, the testing component 4 can be any commonly available image processing device, and is constituted by the image input component 41, which inputs image data outputted from the observation camera 31, the image processor 43, which performs image processing on the inputted image data according a preprogrammed sequence, the categorical testing component 44, which compares a predetermined test standard against the data outputted from the image processor 43 and performs testing by category, and the test result output component 45, which outputs the results of testing by category.

The image processor 43 comprises a binary processor 43a, a binary measuring component 43b, and a region recognition component 43c.

The binary processor 43a binarizes the image data acquired by the image input component 41, and extracts the bright tape portion as a white image, and the dark underlying tape layer as a black image. The binary measuring component 43b computes the surface area, width, length, direction, and so forth for each clump of white portion, for the image data binarized into black and white by the binary processor 43a.

The region recognition component 43c recognizes as a tape portion any clump of white portion that falls within a specific range of surface area, width, length, and direction, and recognizes as a test region any region in which this tape portion is present. The region recognition component 43c performs circumscribing rectangular fitting processing, for example, on each range recognized as a tape portion. This circumscribing rectangular fitting processing involves performing fitting processing based on the least squares method so that a clump of white portion recognized as a tape portion will be circumscribed by a rectangle, and computing the positional coordinates of the ends in the X and Y directions.

More specifically, the image processor 43 is constituted by a combination of the hardware of an image processing device, and an executable program (software) for carrying out the functions of the above-mentioned binary processor 43a, binary measuring component 43b, and region recognition component 43c.

The categorical testing component 44 comprises an end position sensor 44a, a spacing measurement component 44c, a spacing sensor 44d, an overlap sensor 44e, and a foreign matter sensor 44f.

Figure 4A:
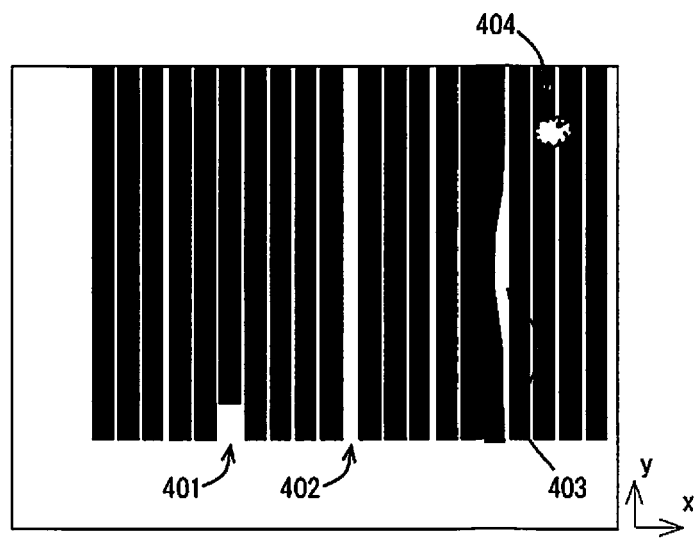
FIGS. 4A and 4B are diagrams of the state when a test object has been observed with the test device pertaining to the present invention.
Figure 4B:
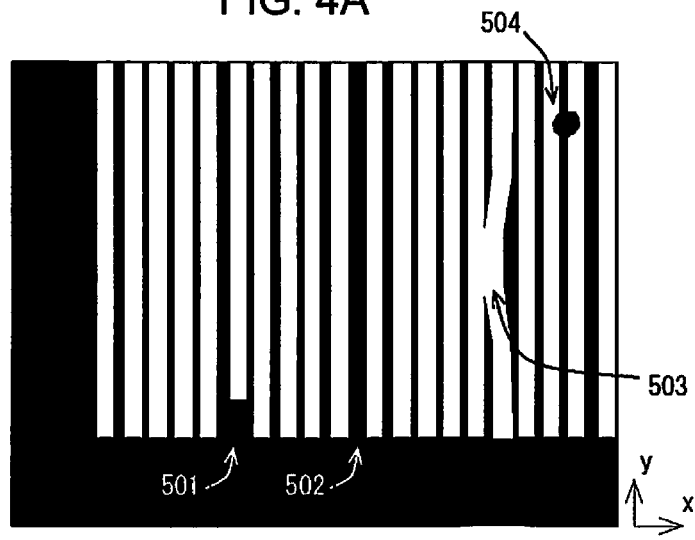

FIGS. 4A and 4B are diagrams of the state when a test object has been observed with the test device pertaining to the present invention, with FIG. 4A showing the test object w1 in the test region f, and FIG. 4B showing a simulation of an observation image. FIG. 4A shows how the various errors listed below occur in the test object w1.

1) The portion indicated by the arrow 401 is an error called "end misalignment," in which the position of one end is offset in the Y direction from the ends of the other tapes.

2) The portion indicated by the arrow 402 is an error called "abnormal gap," in which the spacing between two adjacent tapes in the X direction is wider than the specified value.

3) The portion indicated by the arrow 403 is an error called "abnormal lapping," in which two adjacent tapes overlap one another.

4) The portion indicated by the arrow 404 is an error called "foreign matter adhesion," in which foreign matter adheres to the surface of the tape.

FIG. 4B shows the state when the observation camera 31 has captured an image of the region corresponding to FIG. 4A, and this is outputted as a black and white image by binary processing.

The tape shown in FIGS. 4A and 4B is applied in a state in which the fibers extend in the Y direction, and when the present invention is used to observe the test object w1, the tape portion of the uppermost layer looks white (appears as a bright part), and the tape in underlying layers looks black (appears as a dark part). Accordingly, the portions where tape forming a layer to be tested is applied is displayed in white, and portions where any of the various errors mentioned above have occurred are displayed as follows.

1) At places where an end misalignment error (indicated by the arrow 501) has occurred, the boundary between the white and black portions is offset.

2) At places where an abnormal gap error (indicated by the arrow 502) has occurred, the spacing between black portions is wider.

3) At places where an abnormal lapping error (indicated by the arrow 503) has occurred, there is no black portion, or the spacing of the white portions is close to double the specified width.

4) At places where a foreign matter adhesion error (indicated by the arrow 504) has occurred, a black region has encroached on a region that is supposed to be white.

These errors are detected by the various sensors of the above-mentioned categorical testing component 44.

The end position sensor 44a subjects the positional coordinates of the ends in the Y direction of the various tape portions calculated by the region recognition component 43c to linear approximation, and if there is a circumscribed rectangle around an end position outside of the specified range, it is determined that an "error" has occurred in this tape portion. An end misalignment error can thereby be detected.

The spacing measurement component 44c measures the position of the ends in the X direction of the various tape portions calculated by the region recognition component 43c, and measures the width of the spacing between these tape portions (that is, the X direction of the black portions). The spacing sensor 44d determines that the width of this black portion is "OK" if it falls within a specified value range, and is an "error" if it falls outside this range. This allows abnormal gap errors to be detected. The overlap sensor 44e determines that the width of a white portion is "OK" if it falls within a specified value range, and is an "error" if it falls outside this range. This allows abnormal lapping errors to be detected.

The foreign matter sensor 44f measures the surface area of a black portion that is present in a region of a white portion that has undergone rectangle approximation by the region recognition component 43c, and determines it to be "OK" if there is no black portion larger than a specific surface area, and to be an "error" if there is a black portion larger than a specific surface area. This allows foreign matter adhesion errors to be detected.

More specifically, the categorical testing component 44 is constituted by a combination of the hardware of an image processing device and an executable program (software) for carrying out the functions of the above-mentioned end position sensor 44a, spacing measurement component 44c, spacing sensor 44d, overlap sensor 44e, and foreign matter sensor 44f.

The test result output component 45 outputs errors detected by the categorical testing component 44 to the outside. More specifically, the test result output component 45 is, for example, a signal output component or data transmitter provided to an image processing device, or a signal output unit or data transmission unit connected to an image processing device.

The test device 1 pertaining to the present invention is configured as discussed above, and can favorably sense the application state of the tape forming the uppermost layer. That is, since illuminating light is selected to be emitted from a direction suited to the fiber direction in the fiber reinforced plastic tape, testing can be performed by focusing on the application state of the uppermost layer of tape, without being affected by the fiber direction of underlying layers. Accordingly, testing of the lamination state can be automated, without having to rely on human work, so testing accuracy can be improved and testing expense and duration can be reduced.

Other Embodiments (1)

The test device 1 configured as above can be used to test the application state of fiber reinforced plastic tape, but this testing can also be performed by using a test device 1a in another embodiment. The test device 1a includes the configuration of the above-mentioned test device 1, and further includes a relative movement component 5.

For example, when a flat test object w1 is tested, the relative movement component can be in any of the following forms.

1) The flat test object w1 is left fixed, while the test device 1 side is installed on a slider mechanism with two perpendicular axes. The slider mechanism in this example refers to a mechanism with which a rail that extends linearly, a moving body called a slider that is attached onto this rail, and a mechanism for moving or stopping this slider at a specific location on the rail by using a motor and a ball screw, or a linear motor.

2) When the test device 1 has been fixed, the flat test object w1 is installed on a slider mechanism with two perpendicular axes.

3) The flat test object w1 and the test device 1 are each installed on a uniaxial slider mechanism, and the two uniaxial slider mechanisms are installed perpendicular to each other.

A series of operations is then performed in which the relative movement component 5 is moved to change the location of the test region f on the test object w1 and testing is performed for each test region, and testing is performed over the entire surface of the test object w1. Using the test device 1a configured as above allows the entire surface of the test object w1 to be tested automatically.

Other Embodiments (2)

Meanwhile, for a structure w2 that is a cylindrical test object (hereinafter referred to as the test object w2), the test device 1 can be configured as described below.

Figure 5:
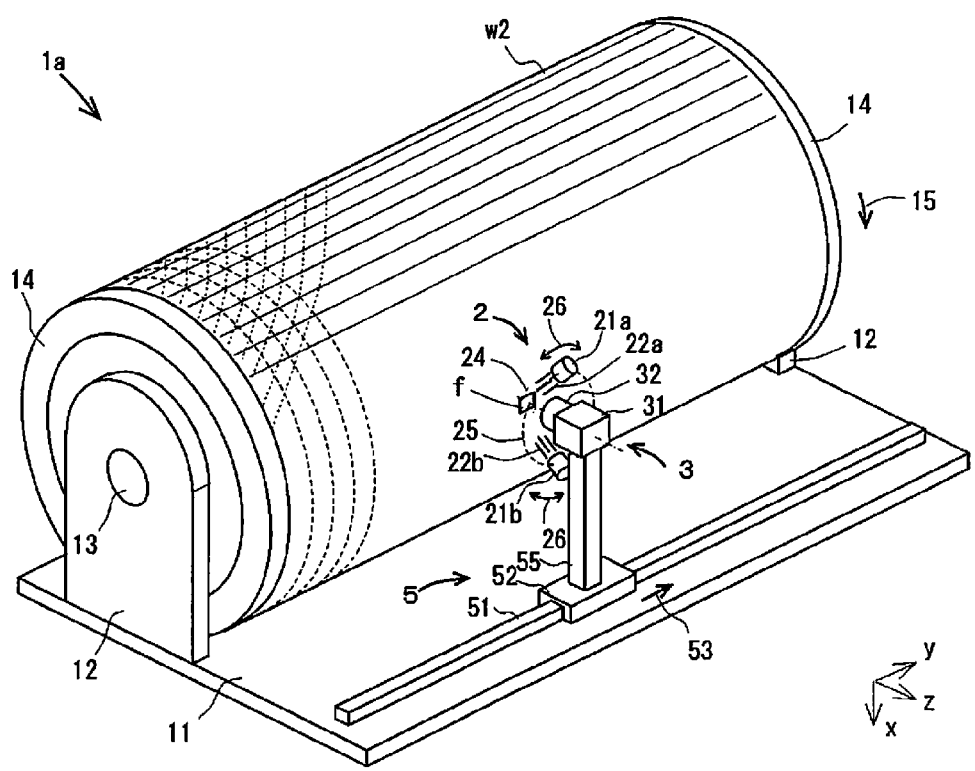
FIG. 5 is an oblique view of the simplified configuration of the test device in another embodiment pertaining to the present invention.

FIG. 5 is an oblique view of the simplified configuration of the test device in another embodiment pertaining to the present invention, and shows an example of an embodiment of testing the test object w2. This test object w2 is produced by laminating a number of layers of fiber reinforced plastic tape on the surface of a cylindrical structure while varying the direction.

The test device 1b in another embodiment includes the configuration of the above-mentioned test device 1, and further includes a relative movement component 5a.

The relative movement component 5a maintains a steady distance between the observation component 3 and the surface of the test object w2 while moving the observation site of the observation component 3 relatively with respect to the test object w2. More specifically, it is configured to include a rail 51 that is disposed parallel to the surface of the test object w2, a slider 52 that can move freely over the rail 51 and stop at a specific location, and a fixing bracket 55 attached on the slider. Consequently, the slider 52 of the relative movement component 5a can maintain a steady distance from the surface of the test object w2, while the illumination component 2 and the observation component 3 can be moved in the direction indicated by the arrow 53.

The test object w2 is supported from both ends of the test object w2, with a support member called a mandrel 14 sandwiched in between. The mandrel 14 is attached so as to be able to rotate around a rotational shaft 13 provided to a support column 12 disposed on the floor or on a plate 11 installed on the floor. A rotational drive motor, a position sensor, a brake mechanism, and so forth (not shown) are attached to the rotational shaft 13, and the test object w2 is clamped and supported by the mandrel 14 and rotated by a specific angle in the direction of the arrow 15, and can be stopped at a specific location.

The relative movement component may be in some other form different from that above, and may be configured so that a multi-articulated robot capable of multiaxial control is used to move relatively over the surface of the test object w2.

Other Embodiments (3)

Also, as discussed above, the irradiation units 21a and 21b are disposed so as to emit the pair of observation-use illuminating light beams 22a and 22b from directions that are symmetrical to each other with respect to a normal line of the test region f. Furthermore, the illumination component 2 comprises an illumination direction change component that changes the direction of the pair of observation-use illuminating light beams 22a and 22b emitted from the irradiation units 21a and 21b about a normal line of the test region f.

The illumination direction change component will be discussed in detail below, but the observation-use illuminating light beams 22a and 22b can be left facing the test region f, while the irradiation units 21a and 21b are rotated and moved in the direction indicated by the arrow 26 along the path indicated by the broken line 25 around the normal line of the test region f, or numerous rows of lighting arranged in the full peripheral direction can be selected by switching. As long as the normal line of the test region f coincides with the observation light axis 35 of the observation component 3, the irradiation units 21a and 21b may be rotated and moved around the observation light axis 35, using the observation light axis 35 of the observation component 3 as the rotational center, for example.

Figure 6A:
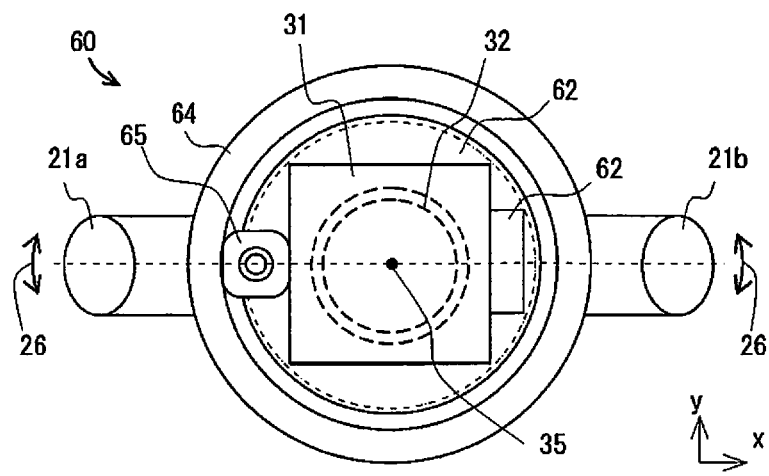
FIGS. 6A and 6B are diagrams of the test device pertaining to the present invention, equipped with an illuminated rotation type of illumination direction change component.
Figure 6B:
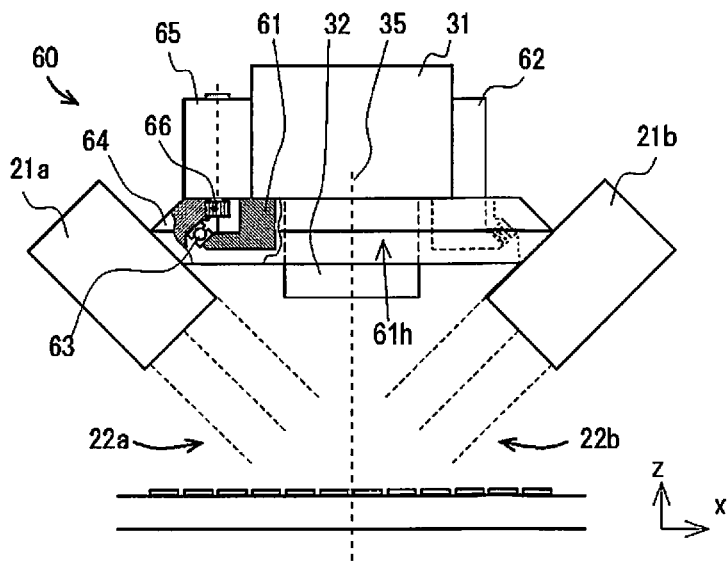

FIGS. 6A and 6B are diagrams of the test device pertaining to the present invention, equipped with an illuminated rotation type of illumination direction change component, FIG. 6A is a plan view, and FIG. 6B is a partial side view corresponding to FIG. 6A.

The test device 1c comprising an illuminated rotation type of illumination direction change component is configured to comprise an illumination holder 60 and an illumination holder rotation component 62 in addition to the configuration of the test device 1 discussed above. Furthermore, the irradiation units 21a and 21b are disposed so as to emit the observation-use illuminating light beams 22a and 22b from at least two directions and toward the test region f.

The illumination holder 60 fixes and holds the irradiation units 21a and 21b at a specific angle. More specifically, it can be embodied by the following configuration. A ring-shaped fixing bracket 61 having a through-hole 61h is readied, and onto this is attached a fixing bracket 62 that holds the observation camera 31. Furthermore, a ring-shaped guide component 63 that can move around the observation light axis 35 is provided to the ring-shaped fixing bracket 61 at a constant distance from the observation light axis 35. This guide component 63 can be embodied as a bearing guide, a curved rail, a continuous groove, or the like. A ring-shaped bracket 64 that can move along the guide component 63 is then disposed, and the irradiation units 21a and 21b are disposed on the ring-shaped bracket 64. The irradiation units 21a and 21b here are disposed so as to emit the observation-use illuminating light beams 22a and 22b from directions that are symmetrical to each other with the observation light axis 35 in between, toward the test region f, and over a range that is wider than the test region f.

The illumination holder rotation component rotates the irradiation units that light simultaneously around the observation light axis 35 of the observation component 3. More specifically, it is embodied by the following configuration. Part of the inner peripheral face of the ring-shaped bracket 64 is made in the form of a gear. Meanwhile, a motor 65 is attached to the ring-shaped fixing bracket 61, and a gear 66 attached to the motor 65 meshes with the inner peripheral face of the ring-shaped bracket 64 that is made in the form of a gear.

By doing this, when the motor 65 is driven, the ring-shaped bracket 64 rotates around the observation light axis 35, and the irradiation units 21a and 21b attached to the ring-shaped bracket 64 rotate and move as a pair in the direction of the arrow 26. Consequently, the direction of the pair of observation-use illuminating light beams 22a and 22b emitted from the irradiation units 21a and 21b that light simultaneously can be changed about the normal line of the test region f.

Other Embodiments (4)

Figure 7A:
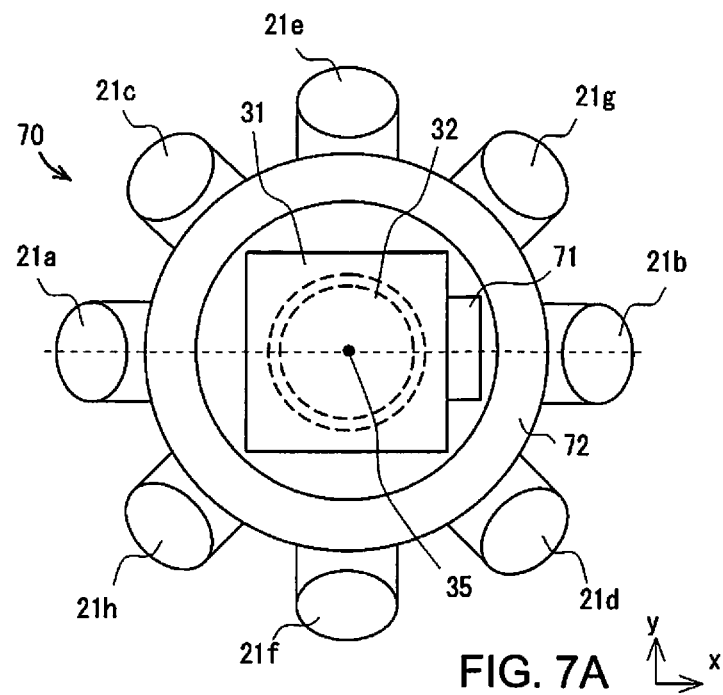
FIGS. 7A and 7B are diagrams of the test device pertaining to the present invention, equipped with an illuminated switching type of illumination direction change component.
Figure 7B:
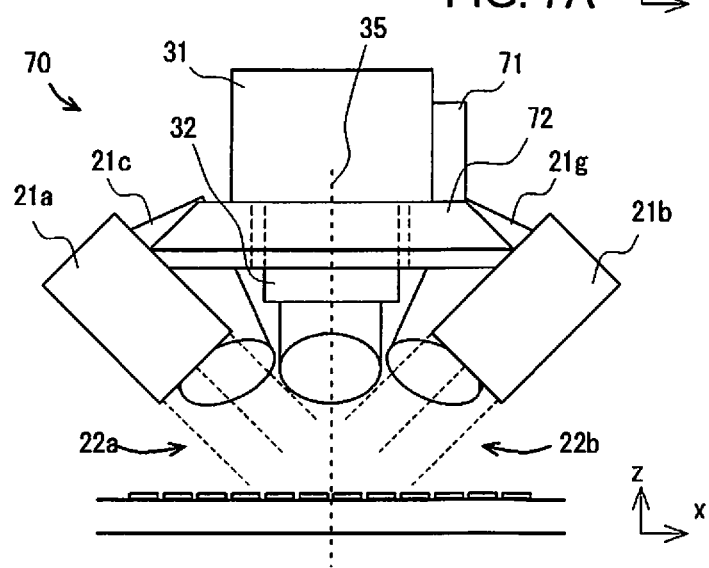

FIGS. 7A and 7B are diagrams of the test device pertaining to the present invention, equipped with an illuminated switching type of illumination direction change component, FIG. 7A is a plan view, and FIG. 7B is a side view corresponding to FIG. 7A. A test device 1d equipped with an illuminated switching type of illumination direction change component is configured as follows.

The illumination component 2 comprises a plurality of irradiation units 21a to 21h, and these are disposed so that observation-use illuminating light beams are emitted from all peripheral directions with respect to the normal line of the test region f, toward the test region f.

The illumination direction change component further comprises a switching component that selectively lights the irradiation units that light simultaneously.

This switching component switches the emission of the observation-use illuminating light beams by selecting at least two specific directions from among all the peripheral directions.

FIGS. 7A and 7B show how the pair of observation-use illuminating light beams 22a and 22b emit from mutually symmetrical directions with respect to the normal line of the test region f, from only the irradiation units 21a and 21b that light simultaneously.

The irradiation units 21a and 21b light simultaneously as a pair. Similarly, irradiation units 21c and 21d, 21e and 21f, and 21g and 21h each light simultaneously as a pair. The switching component selects which of these paired irradiation units are to be lit.

Other Embodiments (5)

With the test device in the above embodiments, as long as the application direction of the uppermost layer of tape that will be the test object is known in advance, the observation-use illuminating light beams can be emitted from a direction perpendicular to this direction, a black-and-white image of sufficient contrast can be acquired as shown in FIG. 4B, and the specified test can be carried out. However, if the application direction of the tape cannot be ascertained in advance, or even if it has been ascertained, if there is actually an offset to the angle, then there is the risk that the acquired image will not have sufficient contrast when a direction of the observation-use illuminating light beams is determined in advance for testing.

Accordingly, in addition to the configuration discussed above, the test device pertaining to the present invention preferably comprises an image recorder, a position sensor, an illumination direction sensor, a continuous observation controller, and a grouping test function.

The image recorder records images observed by the observation component 3.

The position sensor senses the observation site of the observation component 3 with respect to the structure serving as the test object, and is provided to the relative movement component 5.

The illumination direction sensor senses from which direction the observation-use illuminating light beam is emitted with respect to the field of the observation camera 31, and is provided to an illumination direction change component 25.

The continuous observation controller relatively moves the observation site of the observation component with respect to the structure, while continuously observing an image and varying the illumination direction.

The grouping test function groups and tests those continuously observed images that have the same illumination direction.

Figure 8:
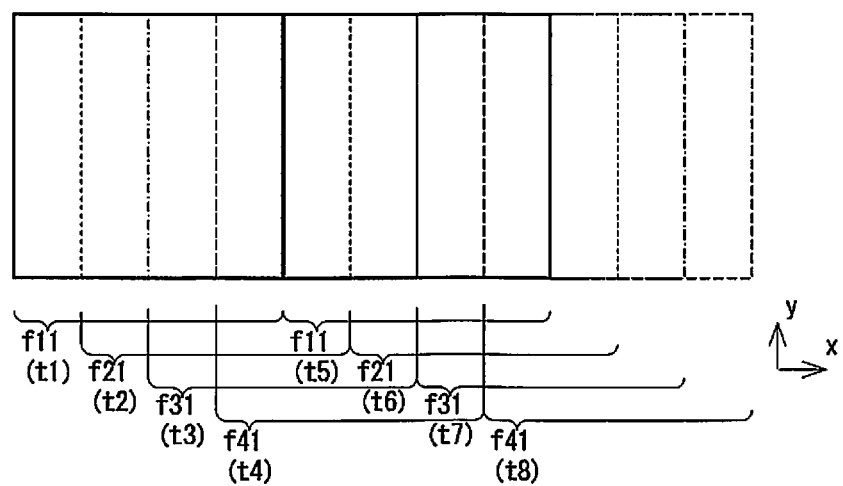
FIG. 8 shows how a test object is continuously observed with the test device pertaining to the present invention.

FIG. 8 shows how a test object is continuously observed with the test device pertaining to the present invention, and shows which site of the test object is being observed for each time change.

That is, at a time t1, the site indicated by f11 is observed as the test region, and at the times t2, t3, and t4, the sites indicated by f21, f31, and f41, respectively, are observed as the test region. At the times t5, t6, t7, and t8, the sites indicated by f12, f22, f32, and f42, respectively, are observed as the test region, with the adjacent test regions being observed in this same manner. Here, the test regions f11, f21, f31, f41, f22, f32, and f42 are observed in a state of being offset in their positions by one-quarter pitch each.

The observation-use illuminating light beams are emitted while the illumination direction is varied as follows.

At the time t1, observation-use illuminating light beam is emitted from a direction perpendicular to the longitudinal direction (as seen in the drawings), and at the times t2, t3, and t4, observation-use illuminating light beam is emitted from directions that are offset clockwise by 45 degrees each from this position. At the time t5, observation-use illuminating light beam is again emitted from a direction perpendicular to the longitudinal direction, and at the times t6, t7, and t8, once again observation-use illuminating light beam is emitted from directions that are offset clockwise by 45 degrees each from this position.

When this is done, an observation image can be obtained with sharp black and white contrast at f11 and f21, at f21 and f22, at f31 and f32, and at f41 and f42, for layers in which the direction in which the fibers extend is zero degrees, 45 degrees, 90 degrees, and 135 degrees, and the same observation can be continued to acquire uninterrupted observation images for the entire surface of the test object, and test the application state of the tape.

Figure 9A:
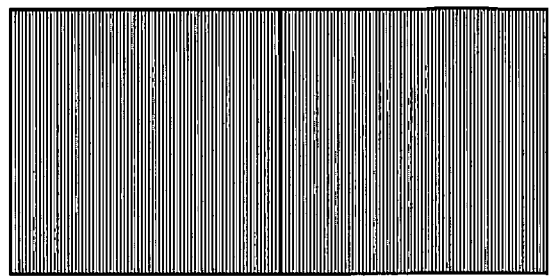
FIGS. 9A, 9B, 9C and 9D are diagrams of the state when a test object is continuously observed with the test device pertaining to the present invention.
Figure 9A:
Figure 9B:
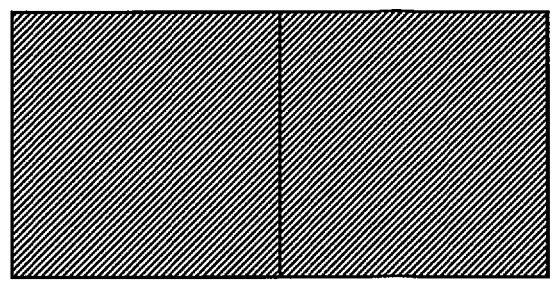
Figure 9B:
Figure 9C:
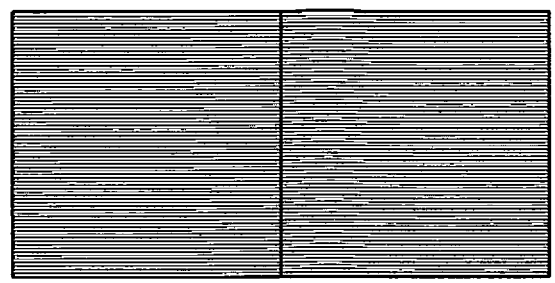
Figure 9C:
Figure 9D:
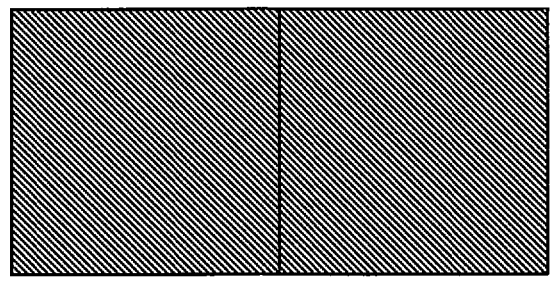
Figure 9D:

FIGS. 9A, 9B, 9C and 9D are diagrams of the state when a test object is continuously observed with the test device pertaining to the present invention. FIG. 9A shows an observation image observed at f11 and f12 when the application direction of the tape (that is, the direction in which the fibers extend) coincides with the longitudinal direction in the drawings (the Y direction) (0 degrees). Observation images observed at other sites appear blackish overall, and only images of low contrast are obtained. FIG. 9B shows an observation image observed at f21 and f22 when the application direction of the tape has been rotated clockwise by 45 degrees with respect to the longitudinal direction in the drawings. Observation images observed at other sites appear blackish overall, and only images of low contrast are obtained (the same applies below). FIG. 9C shows an observation image observed at f31 and f32 when the application direction of the tape has been rotated clockwise by 90 degrees with respect to the longitudinal direction in the drawings. FIG. 9D shows an observation image observed at f41 and f42 when the application direction of the tape has been rotated clockwise by 135 degrees with respect to the longitudinal direction in the drawings.

Images acquired at the times t1 and t5 and images subsequently acquired by the same procedure have the same illumination direction for observation-use illuminating light beam, which is a direction perpendicular to the longitudinal direction in the drawings (zero degrees), and those images in which the illumination direction for observation-use illuminating light beam is the same are tested as a group. Images acquired at the times t2 and t6 and images subsequently acquired by the same procedure have the same illumination direction for observation-use illuminating light beam, which is at 45 degrees to the direction perpendicular to the longitudinal direction in the drawings. Images acquired at the times t3 and t7 and images subsequently acquired by the same procedure have the same illumination direction for observation-use illuminating light beam, which is at 90 degrees to the direction perpendicular to the longitudinal direction in the drawings. Images acquired at the times t4 and t8 and images subsequently acquired by the same procedure have the same illumination direction for observation-use illuminating light beam, which is at 135 degrees to the direction perpendicular to the longitudinal direction in the drawings.

The test device discussed above comprises a grouping test function for grouping and testing images in which the illumination direction of observation-use illuminating light beam is the same, and therefore even if the application direction of the uppermost layer of tape that will be the test object is not known in advance, a black-and-white image of good contrast can still be obtained, and the specified test can be performed. Furthermore, in the above discussion, an example was given in which the test regions were observed after being offset by one-quarter pitch each, and the illumination direction by 45 degrees for each, but the number of divisions may be increased so that the direction of illumination is made more precise. Doing this allows images of sufficiently high contrast to be obtained in testing even when the application angle of the tape ascertained ahead of time undergoes angular offset in actual practice.

Other Embodiments (6)

Figure 10A:
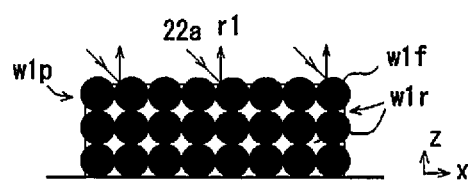
FIGS. 10A, 10B and 10C show how illuminating light of the test device pertaining to the present invention is reflected by a test object.
Figure 10B:
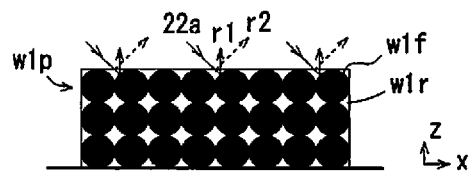
Figure 10C:
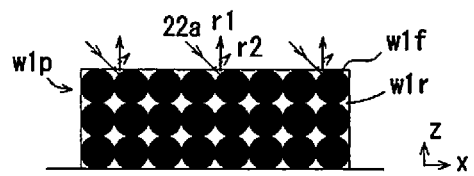

FIGS. 10A, 10B and 10C show how illuminating light of the test device pertaining to the present invention is reflected by a test object. With the test device in the embodiments discussed above, as shown in FIG. 10A, as time passes after a fiber reinforced plastic tape w1p has been applied, the solvent component contained in an impregnating resin w1r volatilizes, and the volume of the resin w1r begins to decrease (known as thinning). When this happens, the observation component 3 observes numerous light beams r1 that are reflected by the surface of the fibers w1f, out of all the observation-use illuminating light beam (22a in the drawing). Accordingly, testing can be favorably carried out by using wavelengths in the visible light band and the ultraviolet band.

As shown in FIG. 10B, however, if there is a large quantity of impregnating resin w1r immediately after the application of the fiber reinforced plastic tape w1p, if we assume that the observation-use illuminating light beam (22a in the drawing) is light with a relatively short wavelength, then light r2 reflected by the surface of the resin w1r will increase, and light r1 reflected by the surface of the fibers w1f will end up decreasing, so the contrast of the observation image will tend to decrease. Accordingly, it is preferable if the observation-use illuminating light beam includes light with a wavelength of at least 600 nm, and if the observation component 3 observes light with a wavelength of at least 600 nm out of the reflected light r. More specifically, examples include the use of light from an incandescent lamp, a halogen lamp, an infrared LED, a laser, or the like for the observation-use illuminating light beam.

If this is done, as shown in FIG. 10C, if we assume that the observation-use illuminating light beam (22a in the drawing) is light with a relatively long wavelength, then the light will more readily pass through the surface of the resin w1r, the light r2 reflected by the surface of the resin w1r will decrease, and the light r1 reflected by the surface of the fibers w1f will increase, so the contrast of the observation image will be higher. This means that binary processing with the image processor 43 will be easier, test accuracy will be increased, and the testing will take less time.

Other Embodiments (7)

With the test device in Embodiment (6) above, light with a wavelength of at least 600 nm is emitted for observation, so more light is reflected from the fiber surface. If light of less than 600 nm is emitted, however, there is a limit to how much the contrast can be raised. Accordingly, the observation component 3 more preferably comprises a filter that attenuates light with a wavelength of 600 nm or less, out of the reflected light r. In this case, light of a relatively short wavelength reflected by the resin surface is cut out, so just the light reflected by the surface of the fibers can be efficiently observed, which means that the contrast of the observation image will be much higher. Accordingly, binary processing with the image processor 43 will be much easier, test accuracy will be further increased, and the testing time will be even shorter.

Other Embodiments (8)

With the test devices in the above embodiments, light was emitted from a specific direction, but various polarized light components were emitted from various light sources. Accordingly, if the resin impregnating the fiber reinforced plastic tape should thin out over time after the tape is applied, then out of the observation-use illuminating light beams, only the light component having a polarization direction that is the same as the direction in which the fibers extend will be reflected by the fiber surface. However, immediately after the fiber reinforced plastic tape has been applied, if there is a large quantity of impregnating resin, and if this resin has reflectivity of a light component with a relatively long wavelength, and reflected light of the scattered component including various polarization directions is observed by the observation component 3, it will be difficult to obtain an image of the desired contrast.

Accordingly, more preferably the observation component 3 further comprises a polarizing filter and a polarizing filter holder that holds the polarizing filter, and the polarizing filter holder comprises a polarization direction adjustment component that adjusts the polarization direction of the polarizing filter with respect to the observation light axis 35.

In this case, the polarization direction of the polarizing filter is set to be the same as the direction in which the fibers extend in the fiber reinforced plastic tape of the layer that will be the test object, and reflected light in this polarization direction is selected for observation, so reflected light in other polarization directions (noise component) is cut out, resulting in much higher contrast of the observation image. Accordingly, binary processing with the image processor 43 is much easier, test accuracy is further increased, and the testing time is shorter.

Other Embodiments (9)

With the test device in the above embodiments, the configuration is such that a test result for each test category is outputted from the test result output component 45. If the formation is continued in this state at a place where any of the various errors mentioned above has occurred, there will be a drop in the strength of the formed article. Accordingly, a series of tests is performed prior to form the next layer. At a place where an error has occurred, the tape that caused the error is peeled off, a new tape is applied, and repair is performed to remove any foreign matter, etc.

Therefore, the test device pertaining to the present invention preferably further comprises a function for indicating a defect position, which points out in which portion of the test object the error has occurred, for test categories and test results in the testing component 4. Here, the test category in which the error has occurred and the position thereof, may be indicated, or the test category in which the error has occurred may be combined with the test result, or just a message that some kind of error has occurred and the position thereof may be indicated. Examples of embodiments of pointing out a defect position include displaying on a display device connected to the testing component by using a matrix-form address set on the test object, or fully or partially mapping the test object and displaying, on a display device connected to the testing component, where the defect is located, or simultaneously pointing out one or more sites when an error has actually occurred by using a laser pointer or the like.

When this is done, this saves time and effort that would be entailed by looking for the place to be repaired, and allows the repair processing to be performed quickly, after the tape application step for a given layer is finished. As a result, there is less waiting time until moving on to the tape application step for the next layer.

When an error has occurred as above, there will be situations in which it is preferable for a history to be stored for the test category or test results, and feedback to be provided to management information for the previous step, or for history management to be performed after the shipment of the finished product for the sake of traceability. Therefore, the test device pertaining to the present invention preferably further comprises a test result storage component for storing test categories or test results outputted from a test result output component. Doing this allows history to be managed, and allows feedback to be provided to management information for the previous step, or traceability to be ensured after production shipment.

The invention claimed is:

1. A device for testing an application state of a plurality of strips of fiber reinforced plastic tape affixed in rows on a surface of a structure, the device comprising:
   an illumination component including a plurality of irradiation units configured to emit observation-use illuminating light beams toward a test region of the fiber reinforced plastic tape;
   an observation component configured to observe reflected light from the test region;
   a testing component configured to test the application state of the fiber reinforced plastic tape based on images observed by the observation component;
   a continuous observation controller configured to change an illumination direction and observe the images continuously while relatively moving an observation site of the observation component with respect to the structure; and
   a grouping test function configured to group and test the images that are continuously observed having the same illumination direction of the observation-use illuminating light, the plurality of irradiation units that light simultaneously and are disposed such that a pair of the observation-use illuminating light beams are emitted from directions that are mutually symmetrical with respect to a normal line of the test region, and so as to emit the observation-use illuminating light beams in at least two directions toward the test region, the illumination component including an illumination direction change component that changes the directions of the pair of observation-use illuminating light beams emitted from the illumination component about the normal line.

2. The device for testing the application state of fiber reinforced plastic tape according to claim 1, further comprising a relative movement component configured to keep distance between the observation component and the surface of the structure constant while relatively moving an observation site of an observation component with respect to the structure.

3. The device for testing the application state of fiber reinforced plastic tape according to claim 1, wherein the illumination direction change component further includes an illumination holder that fixedly holds the irradiation units that light simultaneously at a specific angle, and the illumination holder includes an illumination holder rotation component that rotates the irradiation units that light simultaneously around the normal line.

4. The device for testing the application state of fiber reinforced plastic tape according to claim 1, wherein the illumination component is disposed so as to emit light from a peripheral direction with respect to the normal line toward the test region, the illumination direction change component further includes a switching component that selectively lights the plurality of irradiation units that light simultaneously, and the switching component switches the observation-use illuminating light beams by selecting at least two specific directions from the peripheral direction.

5. The device for testing the application state of fiber reinforced plastic tape according to claim 2, further comprising an image recorder configured to record the images observed by the observation component, the relative movement component further including a position sensor that senses the observation site of the observation component with respect to the structure, and the illumination direction change component further including an illumination direction sensor.

6. The device for testing the application state of fiber reinforced plastic tape according to claim 1, wherein the observation-use illuminating light beams includes light with a wavelength of 600 nm or more, and the observation component observes light with a wavelength of 600 nm or more out of the reflected light.

7. The device for testing the application state of fiber reinforced plastic tape according to claim 6, wherein the observation component further includes a filter that attenuates light with a wavelength of 600 nm or less out of the reflected light.

8. The device for testing the application state of fiber reinforced plastic tape according to claim 1, wherein the observation component further includes a polarizing filter and a polarizing filter holder that holds the polarizing filter, and the polarizing filter holder includes a polarization direction adjustment component that adjusts a polarization direction of the polarizing filter around an observation optical axis of the observation component.

9. The device for testing the application state of fiber reinforced plastic tape according to claim 8, further comprising a function for indicating a defect position for test categories in the testing component.

10. The device for testing the application state of fiber reinforced plastic tape according to claim 2, wherein the illumination direction change component further includes an illumination holder that fixedly holds the irradiation units that light simultaneously at a specific angle, and the illumination holder includes an illumination holder rotation component that rotates the irradiation units that light simultaneously around the normal line.

11. The device for testing the application state of fiber reinforced plastic tape according to claim 2, wherein the illumination component is disposed so as to emit light from a peripheral direction with respect to the normal line toward the test region, the illumination direction change component further includes a switching component that selectively lights the plurality of irradiation units that light simultaneously, and the switching component switches the observation-use illuminating light beams by selecting at least two specific directions from the peripheral direction.

12. The device for testing the application state of fiber reinforced plastic tape according to claim 3, further comprising an image recorder configured to record images observed by the observation component, the relative movement component further including a position sensor that senses the observation site of the observation component with respect to the structure, and the illumination direction change component further including an illumination direction sensor.

13. The device for testing the application state of fiber reinforced plastic tape according to claim 4, further comprising an image recorder configured to record images observed by the observation component, the relative movement component further including a position sensor that senses the observation site of the observation component with respect to the structure, and the illumination direction change component further including an illumination direction sensor.

14. The device for testing the application state of fiber reinforced plastic tape according to claim 2, wherein the observation-use illuminating light beams includes light with a wavelength of 600 nm or more, and the observation component observes light with a wavelength of 600 nm or more out of the reflected light.

15. The device for testing the application state of fiber reinforced plastic tape according to claim 3, wherein the observation-use illuminating light beams includes light with a wavelength of 600 nm or more, and the observation component observes light with a wavelength of 600 nm or more out of the reflected light.

16. The device for testing the application state of fiber reinforced plastic tape according to claim 4, wherein
the observation-use illuminating light beams includes light with a wavelength of 600 nm or more, and
the observation component observes light with a wavelength of 600 nm or more out of the reflected light.

17. The device for testing the application state of fiber reinforced plastic tape according to claim 5, wherein
the observation-use illuminating light beams includes light with a wavelength of 600 nm or more, and
the observation component observes light with a wavelength of 600 nm or more out of the reflected light.

18. The device for testing the application state of fiber reinforced plastic tape according to claim 14, wherein
the observation component further includes a filter that attenuates light with a wavelength of 600 nm or less out of the reflected light.

19. The device for testing the application state of fiber reinforced plastic tape according to claim 2, wherein
the observation component further includes a polarizing filter and a polarizing filter holder that holds the polarizing filter, and
the polarizing filter holder includes a polarization direction adjustment component that adjusts a polarization direction of the polarizing filter around an observation optical axis of the observation component.

20. The device for testing the application state of fiber reinforced plastic tape according to claim 19, further comprising
a function for indicating a defect position for test categories in the testing component.

* * * * *